United States Patent [19]

Dietsche et al.

[11] 4,256,894

[45] Mar. 17, 1981

[54] PREPARATION OF CHLORINATED PYRIDINES

[75] Inventors: Thomas J. Dietsche, Berkeley; Jim Love, Walnut Creek, both of Calif.

[73] Assignee: The Dow Chemical Company, Midland, Mich.

[21] Appl. No.: 16,646

[22] Filed: Mar. 1, 1979

Related U.S. Application Data

[63] Continuation-in-part of Ser. No. 899,675, Apr. 24, 1978, abandoned.

[51] Int. Cl.³ .......................................... C07D 213/26
[52] U.S. Cl. .................................................. 546/345
[58] Field of Search ...................................... 546/345

[56] References Cited

U.S. PATENT DOCUMENTS

| 3,418,323 | 12/1968 | Johnston et al. | 546/345 |
| 3,538,100 | 11/1970 | Smith | 546/345 |
| 3,732,230 | 5/1973 | Brewer et al. | 546/180 |

FOREIGN PATENT DOCUMENTS 957276  5/1964  United Kingdom ................ 546/345

Primary Examiner—Alan L. Rotman
Attorney, Agent, or Firm—J. W. Ambrosius

[57] ABSTRACT

Symmetrical tetrachloropyridine, pentachloropyridine and poly-chloro derivatives of 2-chloro-6-(trichloromethyl)pyridine are prepared by reacting a chloro-substituted (trichloromethyl)pyridine in the liquid state with chlorine at temperatures of from at least about 160° C. and in the presence of an amount of a catalyst effective to catalyze the reaction.

29 Claims, 6 Drawing Figures

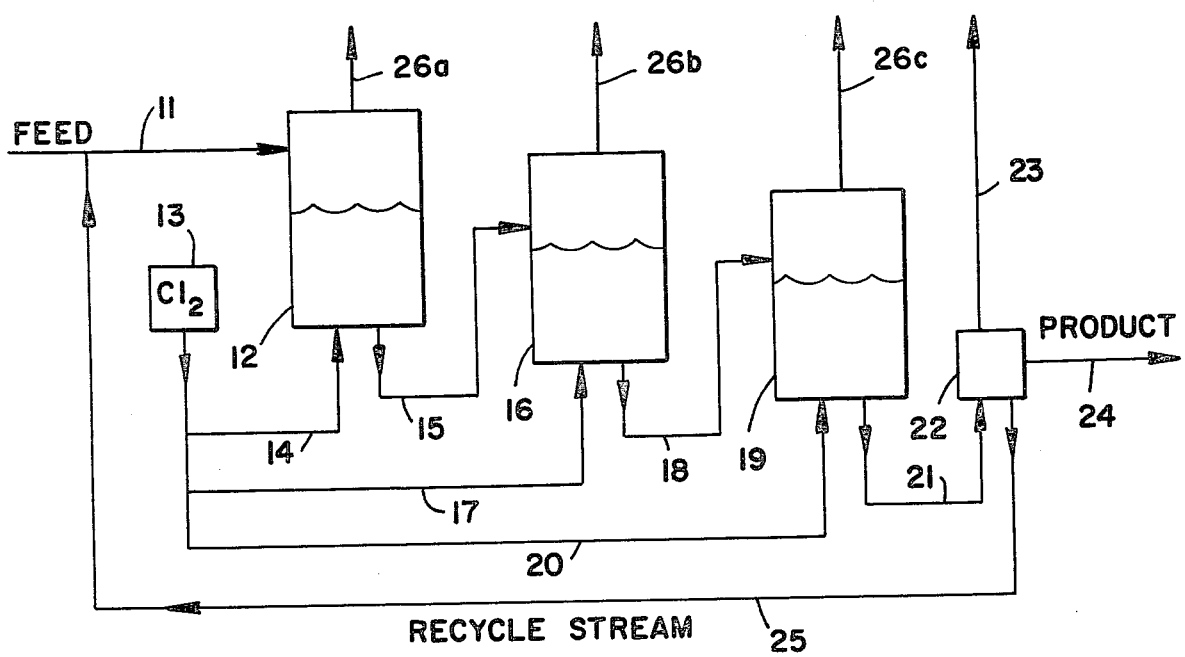
FIG_1
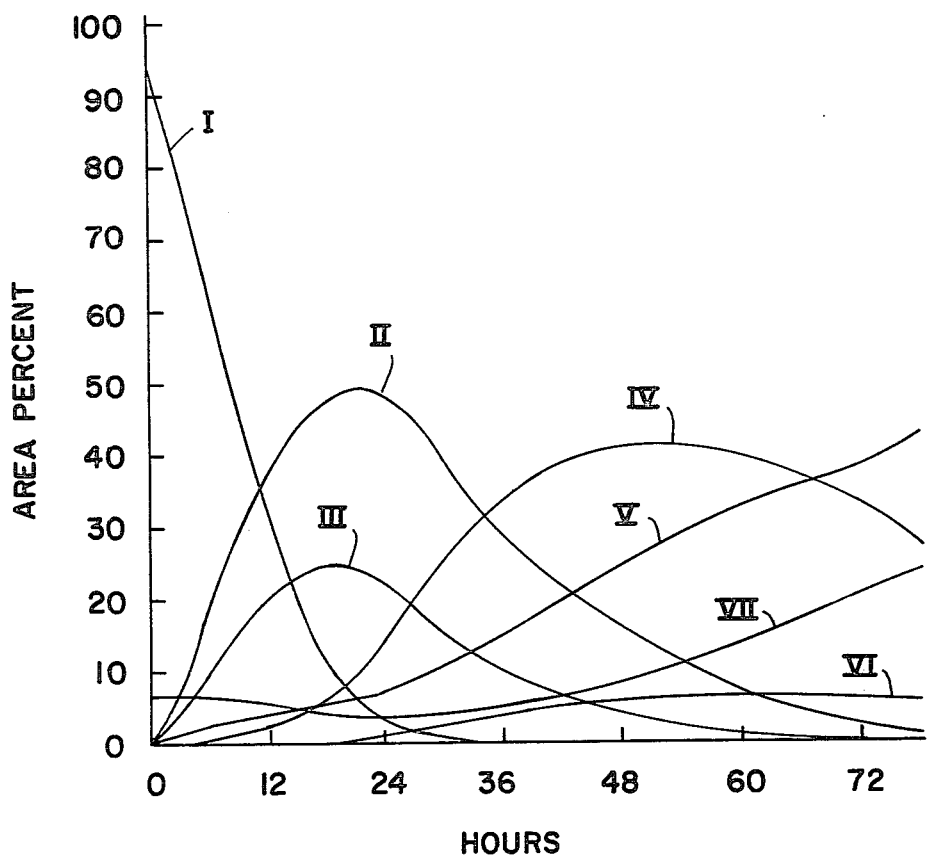
FIG_2

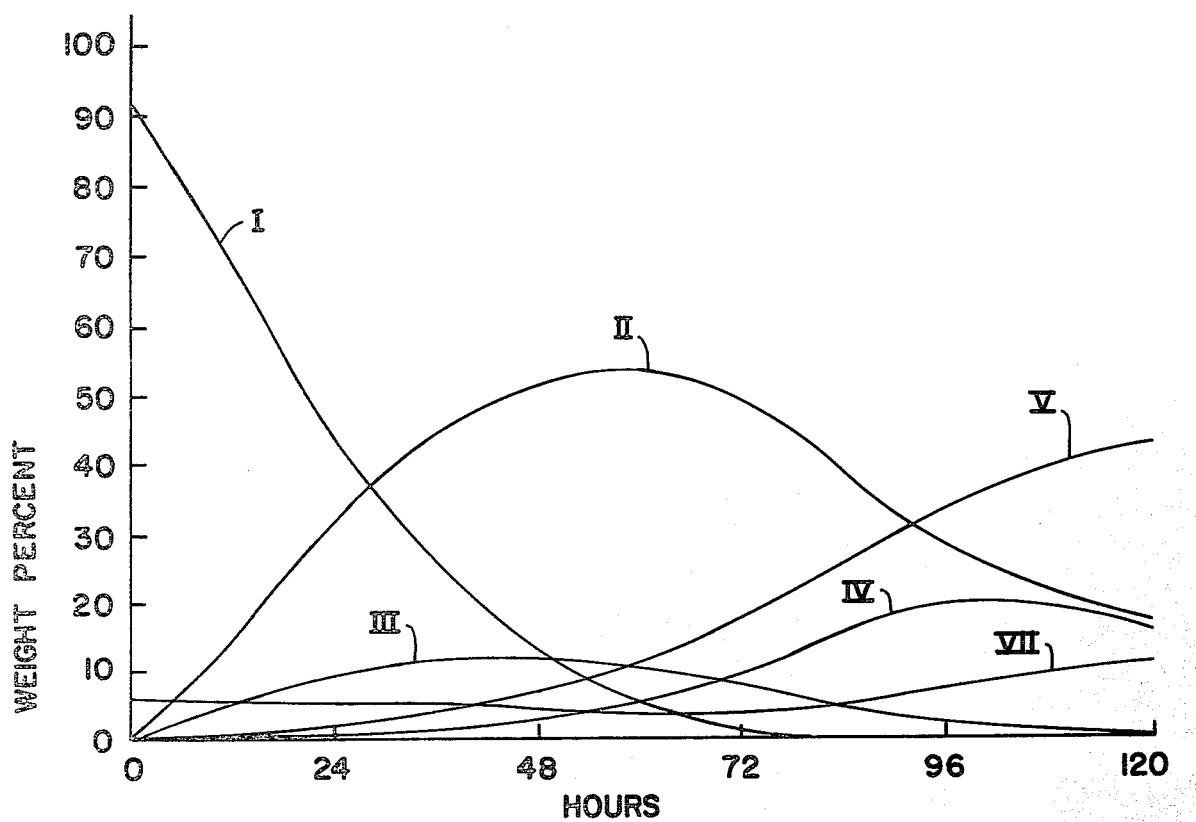
FIG_3
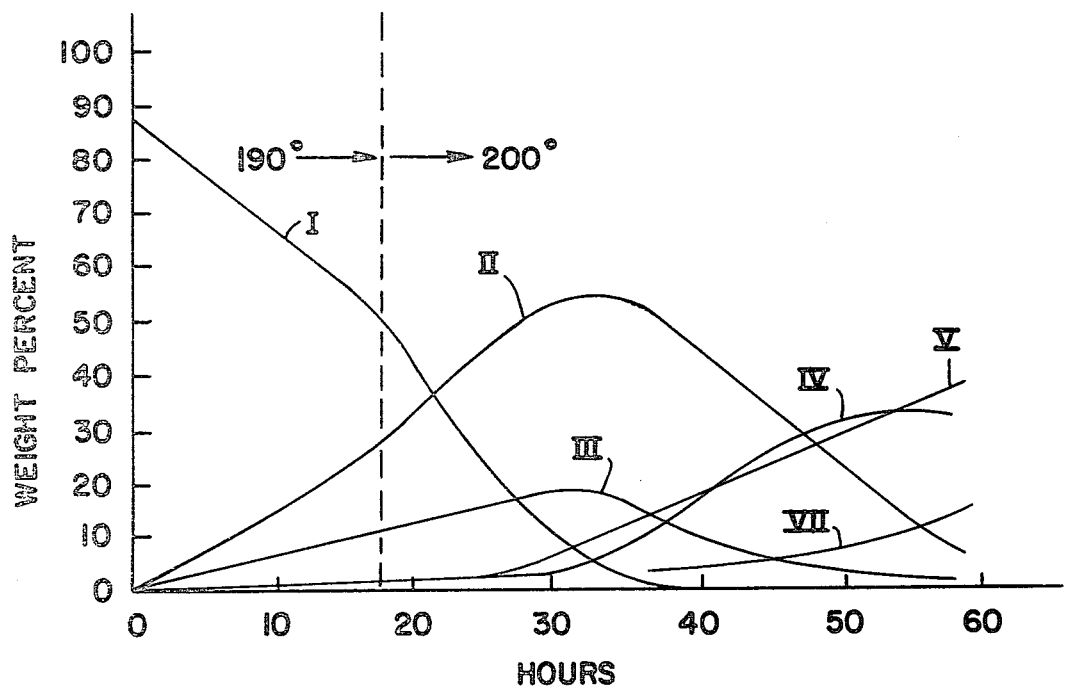
FIG_4

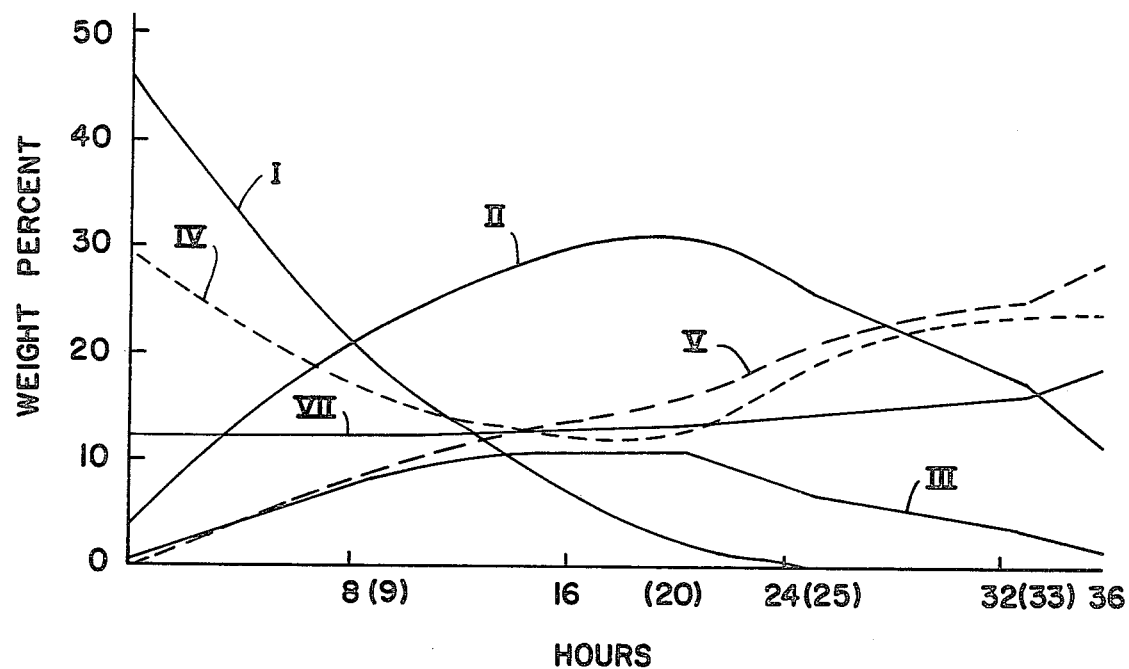
FIG_5
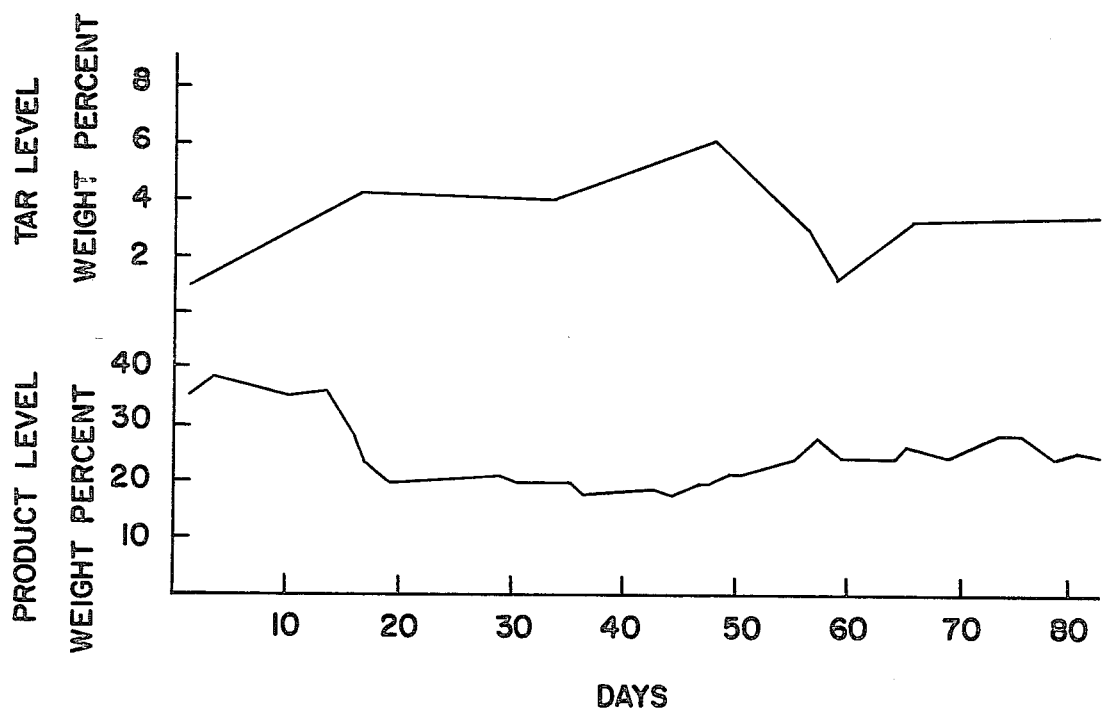
FIG_6

PREPARATION OF CHLORINATED PYRIDINES

CROSS-REFERENCE TO RELATED APPLICATION

This application is a continuation-in-part of our copending application Ser. No. 899,675, filed Apr. 24, 1978, now abandoned.

BACKGROUND OF THE INVENTION

The present invention concerns the preparation of chlorinated pyridine derivatives and particularly concerns the preparation of 2,3,5,6-tetrachloropyridine and 2,3,4,5,6-pentachloropyridine. Chloro-substituted derivatives of 2-chloro-6-(trichloromethyl)pyridine are also prepared according to the present invention.

The chlorinated pyridine derivatives of the present invention are known compounds having been previously prepared by a number of processes. These compounds have uses such as herbicides, pesticides, etc., and are also employed as chemical intermediates in the preparation of other highly desired herbicide or pesticide products. Previous methods for preparing such compounds include those described in U.S. Pat. Nos. 3,538,100 and 3,186,994 and the prior art noted therein. Thus, according to the U.S. Pat. No. 3,538,100 pentachloropyridine and 2,3,5,6-tetrachloropyridine (hereinafter referred to for convenience as "Penta" and "Tetra" products, respectively,) have been prepared by chlorination of liquid 2,6-dichloropyridine at temperatures of at least about 180° C. and in the presence of a metallic halide catalyst. Polychloropyridines, including Penta and Tetra products, are also produced according to the U.S. Pat. No. 3,186,994 by chlorinating in the absence of a catalyst, a polychloro-(trichloromethyl)-pyridine reactant in the liquid state at a temperature of at least 160° C., preferably under irradiation with ultraviolet light.

SUMMARY OF THE INVENTION

It has been discovered that tetra and penta pyridine products and other polychloro pyridine products of the formula:

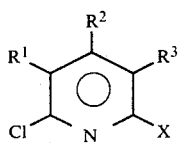

(A)

wherein X represents chloro or —CCl$_3$, R$^1$, R$^2$ and R$^3$ each independently represent chloro or H, with the proviso that when X is —CCl$_3$, at least one of R$^1$, R$^2$ or R$^3$ is always Cl and with the further proviso that when X is chloro, one of R$^1$ and R$^3$ is always chloro,
may be prepared by reacting chlorine with a liquid chloro-substituted (trichloromethyl)pyridine reactant of the formula:

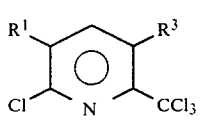

(B)

wherein R$^1$ and R$^3$ are as noted in formula (A).

The formula (B) starting materials, e.g., 2-chloro-, 2,3-dichloro-, 2,5-dichloro- or 2,3,5-trichloro-6-(trichloromethyl)pyridine, are contacted in the liquid state with chlorine at temperatures of at least about 160° C. and at atmospheric pressure or superatmospheric pressures in the presence of a catalyst and an amount thereof effective to catalyze said reaction.

The reaction conditions can be selectively practiced to convert most or part of the trichloromethyl radical to a chloro radical with or without accompanying replacement of hydrogen to produce the desired tetra- and penta-chloropyridines and/or polychloro(trichloromethyl)pyridine compounds. The process of the present invention can also be conducted to provide mixtures of different halogenated pyridines and/or halogenated (trichloromethyl)pyridines, which can be readily separated, or to provide optimum amounts of the highly desired tetra pyridine compound, e.g., 2,3,5,6-tetrachloropyridine, while minimizing the production of the penta pyridine compound and other polychloro(trichloromethyl)pyridine products. The process of the present invention is preferably conducted under anhydrous conditions, and is preferably carried out in a continuous, cyclical operation to produce the preferred product of symmetrical tetrachloropyridine.

DETAILED DESCRIPTION OF THE INVENTION

In the accompanying drawings, which are more fully referred to in the description following below:

FIG. 1 is a diagrammatic sketch showing apparatus used in what is considered to be the best mode known for practicing the invention.

FIGS. 2 and 3 are graphs illustrating results obtained in the batchwise practice of the invention as described in Example 1—Table A and Example 2—Table B, respectively.

FIGS. 4 and 5 are graphs illustrating results obtainable in the practice of the invention on a recycle basis as described in Example 3 and Tables L and M.

FIG. 6 is a graph which demonstrates the results of an extended recycle run and effect of tar concentration on production of desired symmetrical tetrachloropyridine.

In carrying out the process of the present invention, gaseous chlorine is passed into a liquid chloro-substituted 6-(trichloromethyl)pyridine starting material at a temperature of at least about 160° C. in the presence of a selected catalyst. An equimolar amount of the chlorine gas reactant is employed with from about 0.3 to about 10 excess molar proportions of chlorine per mole of starting material desirably being employed. The continuous passage of excess chlorine gas through the reaction mixture serves not only to supply a large amount of reactant but to sweep out any carbon tetrachloride or hydrogen chloride by-products. The most suitable rate at which the chlorine gas is fed will vary with the reaction temperature, pressure, reaction mixture volume, end-product desired, etc. An excess amount of from about 0.3 to about 5.0 moles of chlorine per hour is usually employed per mole of chloro-substituted 6-(trichloromethyl)pyridine starting reactant.

A catalyst and amount thereof effective to catalyze the reaction of a Formula B reactant with chlorine is required to obtain the products of the present invention and any catalyst which is thus effective and compatible with the process is considered to be within the scope of the present invention. Catalysts which are ineffective in so catalyzing the reaction are, of course, not within the scope of the invention. Representative catalysts include, for example, Lewis acid type catalysts such as metals, metaloxyhalides or metallic halides capable of being converted to covalent metallic chlorides under the conditions of the chlorination reaction of the present invention, as well as non-metal catalysts, such as, for example, tellurium tetrachloride. While tellurium is a non-metal element, those skilled in the art recognize it possesses properties and characteristics of many metals. Metals themselves such as iron, zinc, aluminum, tantalum, and the like can be employed, preferably in the powdered form. Representative covalent metallic chlorides and/or metallic oxychlorides and/or halides which can be converted to the chloride form include those such as ferric chloride, ferric bromide, aluminum chloride, aluminum bromide, antimony pentachloride, molybdenum tri- or penta-chloride of oxytetrachloride, tungsten hexachloride, boron trifluoride, titanic chloride, nickel chloride, zinc chloride, tantalum pentachloride, ruthenium trichloride, niobium pentachloride, copper chloride, chromium trichloride, vanadium trichloride, cobalt chloride, and similar materials.

As will be understood by those skilled in the art, no equivalency in activity or operability of the catalyst materials is to be inferred. While certain catalysts have been found to provide good results over a short reaction period, for example, at atmospheric pressure, others which may be operable may require long reaction time periods which may not be economically feasible to obtain similar results. Further, certain catalysts may be superior when employed at elevated temperatures and/or temperatures. The degree of catalytic activity may also vary depending upon the particular product which is to be produced, the degree of catalyst solubility or miscibility with the starting material, the use of fixed bed versus slurried catalysts, etc. In any event, those skilled in the art can, by routine experimentation according to the teachings of the specification and numerous examples herein, readily determine the optimum catalyst and amount thereof required for any particular product to be made or for any particular set of pressure, temperature or time conditions desired.

Catalysts bonded to inert supports or the use of co-catalysts are also contemplated for use in the present invention. Catalysts preferred for use in the present invention include Lewis acid catalysts. Specific preferred catalysts include ruthenium tantalum, tungsten, molybdenum, niobium, aluminum, zinc and iron metals or their halides. Highly preferred catalysts for use in the present invention include the ferric and aluminum halides, and iron and aluminum metals. A preferred catalyst is ferric chloride. A preferred class of catalysts include those which are soluble or readily dispersible in the molten starting material. The catalysts must be employed in an amount effective to catalyze the reaction, e.g., a catalytic amount, and are usually employed in an amount ranging from about 0.5 to about 20 mole % based on the amount of chlorosubstituted 6-(trichloromethyl)pyridine starting material. Preferably, a catalyst concentration of from about 1.0 to about 10 mole % is employed.

While the prior art noted herein teaches that 2,6-dichloropyridine can be chlorinated in the presence of a metallic halide catalyst to the tetra and penta pyridine compounds, it is noted that the process is preferably performed at atmospheric pressure, the corresponding temperature at such pressure being in the range of 180° to 220° C. Chlorination at higher temperatures can be utilized if pressure, e.g., up to 300 psig, is employed.

Likewise, the preparation of tetra and penta pyridine compounds by the chlorination, in the absence of a catalyst, of a polychloro(trichloromethyl)pyridine reactant, with or without irradiation, is disclosed as being most efficient when atmospheric pressure and chlorination temperatures of about 190°–210° C. are employed. While the desired products of the present invention can be obtained by the chlorination, at atmospheric pressure, of 2-chloro-6-(trichloromethyl)pyridine and other similar reactants in the presence of an effective catalyst at temperatures of from about 160° to about 220° C., it has also been surprisingly discovered that such products can be obtained in a much more efficient and economical manner if the chlorination reaction is carried out at pressures substantially in excess of atmospheric. Moreover, in the preparation of the various products, especially the highly preferred tetra pyridine, it was surprisingly discovered that increases in the production of the same were directly correlated to increases in one or more of the pressure, temperature of catalyst amount parameters. Generally, an increase of 10°–15° in the temperature range has the effect of approximately doubling the reaction rate, while an approximately doubling in the pressure from 100 to 200 or so psig elicits a similar response. Up to certain levels and with certain catalysts, an approximate doubling of the catalyst amount also has been found to approximately double the reaction rate.

Thus, in carrying out the process of the present invention, illustratively described with respect to 2-chloro-6-(trichloromethyl)-pyridine as the starting material, the starting material in molten, e.g., liquid, form is usually added to a reactor previously heated to at least about 100° C. and the reactor purged with nitrogen. An effective catalyst in an amount sufficient to catalyze the reaction is then added and chlorine flow commenced, usually at a sufficient rate to pressure the reactor to about 15 psig, or more. The temperature of the reactor is then slowly increased to at least about 160° C. or more and the reaction maintained until sufficient amounts of the desired pyridine compounds are obtained. Liquid samples from the reactor and vent gases are periodically taken and analyzed by known methods to monitor the course of the reaction. The reaction is terminated by stopping the heating of the reactor and the flow of chlorine thereto and allowing the reactor pressure to drop to atmospheric. Distillation of the reaction product obtained can then be carried out to obtain the desirable products therefrom and the still bottoms can be recovered and re-used in the process.

The reaction process is generally illustrated below, on a batch-wise basis, for the preparation of the desired tetra and penta products:

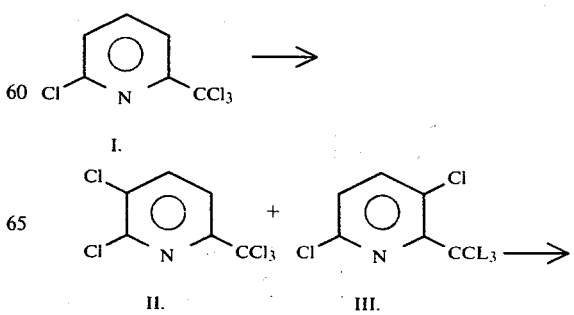

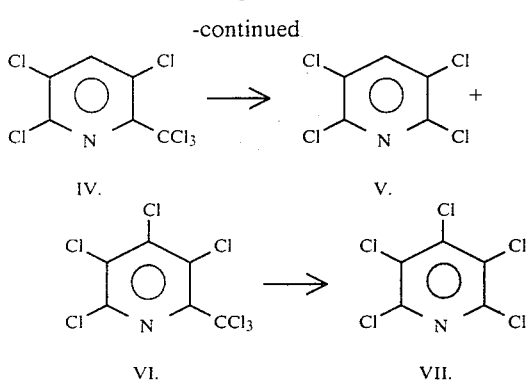

A small amount of 2,6-dichloropyridine (usually less than 0.1%) is sometimes observed in the initial stage of the reaction. However, the same is apparently quickly converted to 2,3,6-trichloropyridine, which subsequently converts to the desired tetra compound, e.g., symmetrical 2,3,5,6-tetrachloropyridine (V). The amount of 2,3,6-trichloropyridine (also partially derived from some of (III)) formed is also minimal, ranging from about 1% at lower reaction temperatures to about 4% at higher temperatures. During the initial stages of the reaction, conversion of the 2-chloro-6-(trichloromethyl)pyridine reactant (I) is largely to the 2,3-dichloro compound (II) with lesser amounts of the 2,5-dichloro compound (III) being formed. Small amounts (e.g., 4–8% by wt.) of 2,4-dichloro-6-(trichloromethyl)pyridine may sometimes be present as an impurity in starting material (I), and this impurity is converted to 2,4,5-trichloro- and 2,3,4-trichloro-6-(trichloromethyl)pyridine products (not illustrated) during the early stages of the reaction and eventually to product (VI). During the formation of the formula (II) and (III) compounds, compounds (IV), (V), (VI) and (VII) are produced in lesser amounts, with the concentrations of products (IV), (V) and (VII) increasing significantly following obtention of peak amounts of compounds (II) and (III). The production of compound (V) continues to increase significantly during the reaction while the concentration of compound (IV) peaks and then begins to diminish. The concentration of compound (VII) continues to increase, although at a lesser rate than compound (V), but will eventually equal and surpass the peak concentration of compound (V) if the reaction is continued for a sufficient period of time.

Those skilled in the art will appreciate that the reaction sequence can thus be conducted in a manner such that products (II), (III) and (IV) can also be obtained as primary products from reactant (I), that materials (II) or (III) can be derived from sources other than (I) and that they can be used to prepare materials (IV) through (VII), and that material (IV) likewise may be obtainable from other methods known in the art and can be utilized as the starting material to prepare products (V) through (VII) according to the present invention. The use of any one or more or mixtures of these as starting materials is to be understood as being embodiments within the scope of the present invention.

Thus, in a first preferred embodiment of the present invention, the process of the present invention is used to prepare 2,3- and 2,5-dichloro-6-(trichloromethyl)pyridine products ((II) and (III)) by reacting chlorine and 2-chloro-6-(trichloromethyl)pyridine (I) at atmospheric pressure and at a temperature of at least about 160° C. in the presence of a catalyst. The optimum amount of product (II) obtained is generally from about 2 to about 4 times the optimum amount of product (III). While products (II) and (III) can be obtained under the conditions noted, the reaction time necessary to obtain significant conversion of the starting material thereto is quite long, e.g., substantially in excess of about 100 hours. Accordingly, for reasons of efficiency and economy, it is preferred that the reaction be carried out at reaction temperatures of at least about 160° C. and under pressures substantially in excess of atmospheric, e.g., from about 15 to about 220 psig or more and a catalyst amount of about 2 mole %. In a highly preferred embodiment, the reaction is carried out at temperatures of from about 160° C. to about 220° C., pressures of about 100 psig to about 220 psig or more and a catalyst amount of about 4 mole % or more, thereby generally obtaining optimum yields of products (II) and (III). In the most preferred embodiment, a reaction temperature of about 200° C., a reaction pressure of about 200 psig and a catalyst amount of from about 1 to about 2–10 mole % are employed. In the latter embodiment, optimum yields of products (II) and (III) can be obtained in a batch reaction in about 10–12 hours. When (II) is the desired product, it is preferred that ruthenium trichloride be employed as the catalyst.

In a second preferred embodiment, the process of the present invention is selectively practised to obtain optimum amounts of product (IV) from starting material (I). Generally, the same reaction temperature and pressure ranges are employed as in the first embodiment, with preferred temperatures of from about 160° to about 220° C., pressures of from about 100 to about 220 psig or more and catalyst amounts of from about 2 to about 10 mole % being employed. Thus, in a particular preferred embodiment, reaction temperatures of from about 180° to about 190° are employed at reaction pressures of from about 190 to about 220 psig.

In a third and highly preferred embodiment of the present invention, the process is employed to obtain optimum amounts of the tetra pyridine compound (V). In such embodiment, the starting material (I) is reacted with chlorine under the same general conditions as set forth in the first embodiment noted above. As noted therein, the reaction can be conducted at atmospheric pressure, but the reaction time necessary to obtain optimum amounts of the product is extremely long. Therefore, it is preferred that the process be carried out at reaction temperatures of from about 160° to about 220° C., preferably from about 180°–210° C., at reaction pressures of from about 15 to about 220 psig or more, preferably from about 100 to about 210 psig, and at catalyst amounts of from about 1 to about 10 mole % or more.

While some product can be obtained when operating at the lower ends of said preferred ranges, for example, 170° and 110 psig, it was discovered that certain increases in one of the temperature, pressure, or catalyst amount parameters greatly affected the reaction time needed to obtain optimum amounts of the tetra compound. Generally, it was found the reaction rate about doubled when the reaction pressure was nearly doubled from 110 to about 200 psig, the reaction temperature (170° C.) and catalyst amount remaining constant. Likewise, a 10°–15° C. increase in the reaction temperature was found to more than double the reaction rate at a constant pressure (200 psig) and catalyst concentration.

Similarly, at constant reaction pressure and temperature, for example, 200 psig and 200° C., the reaction rate was found to be about doubled when the catalyst amount was increased from 2 to 4 mole %. However, the use of larger amounts of catalyst, e.g., generally from about 5 to about 10 mole %, has been found in this and other embodiments to result in an undesirable build-up of tar by-products in the product still bottoms. This increase in tar build-up is particularly undesirable where the same is recycled with still bottoms to form part of the feed starting material. Desirably, the tar level is maintained as low as possible, preferably below about 3 wt. %, based on the starting material of Formula B.

Accordingly, reaction temperatures of from about 180° to about 210° and reaction pressures of from about 190 to about 210 or more psig are preferred; optimum amounts of the tetra pyridine product of from about 25 up to about 40–50 weight percent of the product containing reaction mass can be obtained under such conditions in reaction periods of from about 40 to about 70 hours when using about 2 mole % or more of catalyst. In a highly preferred embodiment, the reaction temperature is about 200° C., the reaction pressure is about 200 psig, and the catalyst is employed in an amount of from about 1 to about 10 mole %.

In all embodiments of the present invention, it is to be noted that the only constraint placed upon the superatmospheric pressures employed is one of economics, and that pressures in excess of the preferred 190–220 psig range may be employed. Those skilled in the art will, however, recognize that the cost factor for pressure equipment to allow operation above 200–220 psig is greatly increased, and that the cost thereof may exceed any benefits obtained.

The 2-chloro-6-(trichloromethyl)pyridine starting material is known and can be prepared according to the methods taught in U.S. Pat. No. 3,420,833. All of the products (II)–(VII), their physical properties, and methods of analysis therefore are known in the art. The interior surfaces of the reactors and inlets, outlets, conduits, etc., should be of materials which resist corrosion by chlorine and hydrogen chloride. Thus, for example, such surfaces may be lined with glass, carbon, nickel, etc.

The following examples illustrate the liquid phase methods but are not to be construed as limiting the invention. The product distribution in all tables is in terms of weight %, unless otherwise indicated.

EXAMPLE 1

A chlorination reactor comprising a 300 ml flask fitted with a sparge tube connected via a rotometer and needle valve to a chlorine source and a condensor connected to a caustic scrubber was charged with a melt (200 grams) of a 2-chloro-6-(trichloromethyl)pyridine starting material. A desired amount of catalyst was then charged to the reactor and the reaction mixture warmed to about 200° C. at atmospheric pressure with stirring and chlorine was sparged into the solution at the rate of about 0.1 mole/hr. Samples were removed via a sampling port at 6 hour intervals. The results (area percent) of operations employing such procedure are set forth below in Table A and illustrated in FIG. 2 hereof:

TABLE A

Temperature: 200° Catalyst: 10.0 mole % Fe
Pressure: Atmospheric

| Sample | Time (hr) | FeCl$_3$ | (I) | (II) | (III) | (IV) | (V) | (VI) | *(VII) | *2,3,4 |
|---|---|---|---|---|---|---|---|---|---|---|
| 0 | 0 | | 93.3 | .3 | — | — | — | — | 6.1 | — |
| 1 | 6 | | 63.0 | 17.5 | 9.2 | .7 | 1.9 | .1 | 6.5 | .8 |
| 2 | 12 | | 32.4 | 35.5 | 18.8 | 2.2 | 3.3 | .2 | 5.5 | 2.1 |
| 3 | 18 | | 10.6 | 47.0 | 24.2 | 5.1 | 4.9 | .4 | 4.2 | 3.7 |
| 4 | 24 | | .6 | 47.6 | 21.7 | 13.9 | 6.6 | 1.1 | 3.1 | 5.3 |
| 5 | 30 | | — | 36.6 | 14.6 | 25.7 | 10.6 | 2.6 | 4.3 | 5.4 |
| 6 | 36 | | — | 30.1 | 9.5 | 32.6 | 14.1 | 3.7 | 5.4 | 4.6 |
| 7 | 42 | | — | 21.4 | 5.9 | 38.0 | 18.9 | 4.8 | 6.8 | 4.1 |
| 8 | 48 | | — | 16.0 | 3.5 | 40.2 | 23.0 | 5.4 | 8.7 | 3.4 |
| 9 | 54 | | — | 10.6 | 1.9 | 40.2 | 27.4 | 5.9 | 11.3 | 2.6 |
| 10 | 60 | | — | 6.3 | .8 | 39.3 | 31.4 | 6.2 | 13.9 | 2.0 |
| 11 | 66 | | — | 4.4 | .5 | 36.6 | 34.6 | 5.9 | 16.3 | 1.6 |
| 12 | 72 | | — | 2.6 | .2 | 33.3 | 36.8 | 6.0 | 19.8 | 1.2 |
| 13 | 78 | | — | 1.4 | .1 | 27.9 | 41.3 | 5.5 | 22.5 | .9 |

*G.C. peak for VII coincides with peak for 2,4-dichloro-6-(trichloromethyl)-pyridine present during early stages of reaction.
**2,3,4-trichloro-6-(trichloromethyl)pyridine.

EXAMPLE 2

A two-liter, 2000 psi Parr reactor with glass liner and equipped with an air driven stirrer is pre-heated to about 100°–125° C. and about one kilogram of a 2-chloro-6-(trichloromethyl)pyridine starting material is melted and poured into the warm reactor and the desired amount of iron powder catalyst is calculated and added to the starting material melt. The reactor is then sealed and chlorine, from a gas cylinder placed in a heated and stirred water bath, is delivered to the liquid phase in the heated reactor via a dip-leg. The pressure of the reaction is regulated by heating the chlorine supply cylinder and the Cl$_2$ flow is regulated at a desired level. The rate of vent gases (Cl$_2$ and HCl) is controlled by a pressure regulator. Once the Cl$_2$ flow is commenced to the stirred liquid reaction mass, the reaction is monitored closely until the desired temperature and gas flow is achieved and temperature, pressure and vent gas flow monitored thereafter on a continuous basis. During the course of the reaction, samples of the reaction mass are periodically taken and analyzed using gas chromatographic (GC) analysis against an internal standard. Once the reaction has reached the desired point of completion, the flow of chlorine is stopped and the heating of the reactor is discontinued. Data set forth in the following tables represent the results of several experimental runs using the above-described procedure. References to products are as designated in the formulas set forth hereinabove.

TABLE B

Temperature: 200° Catalyst: 2.0 mole % Fe
Pressure: 110 psig Vent Gas Flow; 50 ml/min.

| Sample | Time (hr) | FeCl₃ | (I) | (II) | (III) | (IV) | (V) | (VI) | *(VII) | **2,3,4 |
|---|---|---|---|---|---|---|---|---|---|---|
| 0 | 0 | — | 92.2 | .3 | — | — | .2 | — | 5.7 | — |
| 1 | 24 | 1.7 | 43.6 | 32.2 | 9.3 | 1.1 | 1.3 | .2 | 5.2 | 1.0 |
| 2 | 48 | 1.5 | 13.1 | 51.3 | 12.0 | 2.6 | 6.5 | .2 | 4.5 | 2.6 |
| 3 | 72 | 1.4 | 1.1 | 50.2 | 7.6 | 8.9 | 17.6 | .7 | 3.4 | 4.6 |
| 4 | 96 | 1.3 | .1 | 26.7 | 1.5 | 20.0 | 33.3 | 2.2 | 7.2 | 4.2 |
| 5 | 120 | 1.5 | .5 | 17.5 | .6 | 16.2 | 42.5 | 2.1 | 11.1 | 3.5 |
| 6 | 144 | 1.5 | .7 | 18.3 | .5 | 13.1 | 44.8 | 1.9 | 11.8 | 3.8 |

*G.C. peak for VII coincides with peak for 2,4-dichloro-6-(trichloromethyl)-pyridine present during early stages of reaction.
**2,3,4-trichloro-6-(trichloromethyl)pyridine.

TABLE C

Temperature: 200° Catalyst: 2.0 mole % Fe
Pressure: 200 psig Vent Gas Flow: 50 ml/min.

| Sample | Time (hr) | FeCl₃ | (I) | (II) | (III) | (IV) | (V) | (VI) | *(VII) | **2,3,4 |
|---|---|---|---|---|---|---|---|---|---|---|
| 0 | 0 | — | 92.2 | .3 | — | — | .2 | — | 5.7 | — |
| 1 | 12 | 1.7 | 46.4 | 32.3 | 8.0 | 1.0 | .7 | .2 | 5.3 | .8 |
| 2 | 24 | 1.7 | 27.2 | 47.1 | 9.5 | 1.9 | 2.6 | .3 | 5.1 | 1.5 |
| 3 | 36 | 1.7 | 9.5 | 56.7 | 10.0 | 3.2 | 6.5 | .3 | 4.1 | 2.7 |
| 4 | 48 | 1.7 | 1.7 | 57.6 | 8.2 | 6.5 | 12.4 | .6 | 3.1 | 4.2 |
| 5 | 60 | 1.7 | .4 | 48.2 | 4.1 | 12.7 | 20.1 | 1.1 | 3.6 | 5.0 |
| 6 | 72 | 1.8 | .4 | 36.4 | 1.6 | 18.8 | 26.4 | 1.9 | 5.4 | 4.6 |
| 7 | 87 | 1.8 | .4 | 20.5 | .5 | 20.9 | 36.6 | 2.4 | 8.9 | 3.4 |

*G.C. peak for VII coincides with peak for 2,4-dichloro-6-(trichloromethyl)-pyridine present during early stages of reaction.
**2,3,4-trichloro-6-(trichloromethyl)pyridine.

TABLE D

Temperature: 170° Catalyst: 2.0 mole % Fe
Pressure: 200 psig Vent Gas Flow: 150 ml/min.

| Sample | Time (hr) | FeCl₃ | (I) | (II) | (III) | (IV) | (V) | (VI) | *(VII) | **2,3,4 |
|---|---|---|---|---|---|---|---|---|---|---|
| 0 | 0 | — | 92.2 | .3 | — | — | .2 | — | 5.7 | — |
| 1 | 8.5 | | 74.2 | 9.2 | 3.4 | .5 | .3 | .2 | 5.1 | .2 |
| 2 | 16 | 1.5 | 68.1 | 14.3 | 5.0 | .9 | .3 | .4 | 5.3 | .3 |
| 3 | 24 | | 59.3 | 20.4 | 7.1 | 1.3 | .3 | .5 | 5.0 | .5 |
| 4 | 32 | | 49.5 | 28.0 | 9.6 | 1.8 | .4 | .7 | 4.8 | .7 |
| 5 | 40 | 1.7 | 41.6 | 31.7 | 10.9 | 1.9 | .7 | .8 | 4.5 | .8 |
| 6 | 56 | | 25.3 | 42.6 | 15.5 | 3.0 | 1.2 | 1.1 | 3.9 | 1.4 |
| 7 | 68 | | 17.9 | 47.6 | 17.4 | 3.8 | 1.7 | 1.1 | 3.6 | 1.7 |
| 8 | 84 | | 6.3 | 54.4 | 20.0 | 6.1 | 3.3 | 1.3 | 2.7 | 2.6 |
| 9 | 92 | | 2.5 | 53.6 | 19.6 | 8.5 | 4.3 | 1.7 | 2.1 | 3.0 |
| 10 | 104 | 1.6 | .5 | 48.6 | 16.8 | 14.8 | 6.0 | 2.1 | 1.6 | 3.4 |
| 11 | 118 | | .3 | 39.9 | 12.2 | 24.1 | 8.4 | 3.0 | 2.0 | 3.2 |
| 12 | 128 | | .3 | 35.4 | 9.6 | 29.4 | 9.7 | 3.7 | 2.2 | 3.0 |
| 13 | 143 | | .1 | 27.2 | 6.3 | 37.6 | 11.7 | 4.7 | 2.8 | 2.8 |
| 14 | 152 | | .1 | 22.1 | 4.6 | 41.7 | 13.1 | 5.3 | 3.2 | 2.5 |
| 15 | 184 | .5 | .1 | 8.5 | .9 | 53.9 | 18.0 | 7.6 | 5.8 | 1.5 |
| 16 | 213 | | .1 | 3.4 | .5 | 55.5 | 19.1 | 8.6 | 10.0 | .7 |
| 17 | 237 | | .1 | 3.7 | .1 | 45.8 | 22.1 | 7.8 | 16.7 | .1 |
| 18 | 255 | .4 | .1 | 3.7 | .4 | 34.4 | 29.4 | 5.6 | 21.3 | .4 |

*G.C. peak for VII coincides with peak for 2,4-dichloro-6-(trichloromethyl)-pyridine present during early stages of reaction.
**2,3,4-trichloro-6-(trichloromethyl)pyridine.

TABLE E

Temperature: 185° Catalyst: 4.0 mole % Fe
Pressure: 200 psig Vent Gas Flow: 150 ml/min.

| Sample | Time (hr) | FeCl₃ | (I) | (II) | (III) | (IV) | (V) | (VI) | *(VII) | **2,3,4 |
|---|---|---|---|---|---|---|---|---|---|---|
| 0 | 0 | — | 92.2 | .3 | — | — | .2 | — | 5.7 | — |
| 1 | 14 | —**** | 34.2 | 37.6 | 12.8 | 1.7 | .8 | .4 | 4.3 | 1.0 |
| 1E*** | 14 | | 36.2 | 38.7 | 13.2 | 1.8 | .8 | .5 | 4.3 | 1.0 |
| 2 | 28 | — | 13.7 | 48.4 | 17.0 | 3.6 | 2.6 | .6 | 3.2 | 1.9 |
| 2E | 28 | | 15.1 | 51.4 | 17.6 | 3.7 | 2.9 | .7 | 3.4 | 2.0 |
| 3 | 47 | — | .4 | 43.6 | 9.5 | 18.5 | 13.2 | 1.7 | 2.3 | 3.3 |
| 3E | 47 | | .4 | 45.5 | 9.7 | 18.9 | 13.3 | 1.8 | 2.3 | 3.3 |
| 4 | 71 | — | — | 14.4 | 1.1 | 38.0 | 28.5 | 3.9 | 6.7 | 2.2 |
| 4E | 71 | | — | 15.5 | 1.1 | 39.0 | 28.9 | 4.0 | 6.7 | 2.2 |

TABLE E-continued

Temperature: 185° Catalyst: 4.0 mole % Fe
Pressure: 200 psig Vent Gas Flow: 150 ml/min.

| Sample | Time (hr) | FeCl$_3$ | (I) | (II) | (III) | (IV) | (V) | (VI) | *(VII) | **2,3,4 |
|---|---|---|---|---|---|---|---|---|---|---|
| 5 | 93 | — | — | 2.3 | .1 | 31.7 | 36.5 | 4.3 | 17.3 | .6 |
| 5E | 93 | — | — | 2.6 | .1 | .6 | 36.7 | 4.5 | 17.6 | .6 |

*G.C. peak for VII coincides with peak for 2,4-dichloro-6-(trichloromethyl)-pyridine present during early stages of reaction.
**2,3,4-trichloro-6-(trichloromethyl)pyridine.
***E means FeCl$_3$ extracted from sample.
****Not analyzed.

TABLE F

Temperature: 200° Catalyst: 4.0 mole % Fe
Pressure: 200 psig Vent Gas Flow: 150 ml/min.

| Sample | Time (hr) | FeCl$_3$ | (I) | (II) | (III) | (IV) | (V) | (VI) | *(VII) | **2,3,4 |
|---|---|---|---|---|---|---|---|---|---|---|
| 0 | 0 | — | 92.2 | .3 | — | — | .2 | — | 5.7 | — |
| 1 | 12 | —**** | 12.1 | 47.2 | 16.5 | 3.3 | 4.6 | .5 | 3.4 | 2.1 |
| 1E*** | 12 |  | 12.5 | 48.4 | 16.7 | 3.4 | 4.7 | .5 | 3.4 | 2.2 |
| 2 | 24 | — | .6 | 45.3 | 9.9 | 12.1 | 15.9 | 1.0 | 2.7 | 3.6 |
| 2E | 24 |  | .5 | 48.5 | 10.2 | 12.4 | 16.0 | 1.0 | 2.7 | 3.7 |
| 3 | 40 | — | .1 | 12.7 | .8 | 28.8 | 35.3 | 3.3 | 8.9 | 2.3 |
| 3E | 40 | — | .1 | 14.0 | .8 | 30.0 | 35.4 | 3.3 | 9.0 | 2.3 |
| 4 | 48 | — | .1 | 5.0 | .2 | 25.4 | 40.7 | 3.6 | 14.1 | 1.4 |
| 4E | 48 |  | .1 | 5.8 | .4 | 25.9 | 40.9 | 3.5 | 14.1 | 1.4 |

*G.C. peak for VII coincides with peak for 2,4-dichloro-6-(trichloromethyl)-pyridine present during early stages of reaction.
**2,3,4-trichloro-6-(trichloromethyl)pyridine
***E means FeCl$_3$ extracted from sample.
****Not analyzed.

TABLE G

Temperature: 170° Catalyst: 7.0 mole % Fe
Pressure: 110 psig Vent Gas Flow: 50 ml/min.

| Sample | Time (hr) | FeCl$_3$ | (I) | (II) | (III) | (IV) | (V) | (VI) | *(VII) | **2,3,4 |
|---|---|---|---|---|---|---|---|---|---|---|
| 0 | 0 | — | 92.2 | .3 | — | — | .2 | — | 5.7 | — |
| 1 | 24 | 3.8 | 43.1 | 24.9 | 9.7 | 3.3 | .3 | .5 | 4.0 | .7 |
| 2 | 48 | 7.5 | 24.5 | 34.4 | 13.5 | 3.4 | .7 | .6 | 3.0 | 1.2 |
| 3 | 72 | 4.4 | 11.2 | 45.9 | 17.2 | 4.9 | 1.9 | .7 | 2.6 | 2.0 |
| 4 | 96 | 4.6 | 4.0 | 47.8 | 17.0 | 8.8 | 4.3 | 1.1 | 1.9 | 2.7 |
| 5 | 120 | 4.3 | 1.4 | 44.4 | 13.1 | 16.4 | 6.8 | 1.7 | 1.7 | 2.9 |
| 6 | 144 | 4.7 | .5 | 35.7 | 8.2 | 25.6 | 10.6 | 2.7 | 2.1 | 2.7 |
| 7 | 168 | 2.6 | .2 | 25.5 | 4.4 | 38.4 | 13.6 | 4.0 | 2.9 | 2.4 |
| 8 | 192 | 2.2 | .2 | 15.3 | 2.0 | 46.3 | 16.4 | 4.9 | 4.1 | 1.8 |
| 9 | 221 | 3.3 | .1 | 8.2 | .8 | 49.0 | 19.2 | 5.7 | 5.9 | — |
| 10 | 245 | 2.2 | — | 4.7 | .4 | 49.4 | 22.5 | 6.1 | 7.9 | — |

*G.C. peak for VII coincides with peak for 2,4-dichloro-6-(trichloromethyl)pyridine present during early stages of reaction.
**2,3,4-trichloro-6-(trichloromethyl)pyridine.

TABLE H

Temperature: 170° Catalyst: 7.0 mole % Fe
Pressure: 200 psig Vent Gas Flow: 50 ml/min.

| Sample | Time (hr) | FeCl$_3$ | (I) | (II) | (III) | (IV) | (V) | (VI) | *(VII) | **2,3,4 |
|---|---|---|---|---|---|---|---|---|---|---|
| 0 | 0 | — | 92.2 | .3 | — | — | .2 | — | 5.7 | — |
| 1 | 24 | 4.6 | 29.0 | 35.5 | 15.5 | 2.5 | .6 | .5 | 3.4 | 1.1 |
| 2 | 48 | 5.2 | 7.1 | 45.3 | 17.0 | 7.8 | 4.0 | 1.0 | 1.8 | 2.4 |
| 3 | 72 | 5.3 | 2.6 | 41.8 | 10.9 | 15.5 | 9.0 | 1.7 | 1.8 | 2.8 |
| 4 | 96 | 5.3 | 2.4 | 38.5 | 7.5 | 17.0 | 12.2 | 2.0 | 2.3 | 2.8 |
| 5 | 120 | 4.8 | 2.1 | 35.3 | 5.9 | 18.0 | 14.3 | 2.1 | 2.7 | 2.9 |

*G.C. peak for VII coincides with peak for 2,4-dichloro-6-(trichloromethyl)pyridine present during early stages of reaction.
**2,3,4-trichloro-6-(trichloromethyl)pyridine.

TABLE I

Temperature: 185° Catalyst: 7.0 mole % Fe
Pressure: 200 psig Vent Gas Flow: 150 ml/min.

| Sample | Time (hr) | FeCl$_3$ | (I) | (II) | (III) | (IV) | (V) | (VI) | *(VII) | **2,3,4 |
|---|---|---|---|---|---|---|---|---|---|---|
| 0 | 0 | —*** | 92.2 | .3 | — | — | .2 | — | 5.7 | — |

TABLE I-continued

Temperature: 185° Catalyst: 7.0 mole % Fe
Pressure: 200 psig Vent Gas Flow: 150 ml/min.

| Sample | Time (hr) | FeCl$_3$ | (I) | (II) | (III) | (IV) | (V) | (VI) | *(VII) | **2,3,4 |
|---|---|---|---|---|---|---|---|---|---|---|
| 1 | 12 | — | 3.1 | 46.6 | 21.8 | 9.8 | 2.6 | .8 | 1.6 | 2.9 |
| 2 | 18 | — | 1.5 | 42.0 | 16.6 | 15.8 | 6.3 | 1.4 | 1.7 | 3.0 |
| 3 | 24 | — | .2 | 33.3 | 9.94 | 24.4 | 12.3 | 2.1 | 2.2 | 2.8 |
| 4 | 31 | — | .1 | 19.3 | 3.0 | 37.1 | 21.0 | 3.6 | 3.8 | 2.3 |
| 5 | 42 | — | — | 5.8 | .3 | 46.6 | 26.2 | 5.3 | 8.1 | 1.2 |

*G.C. peak for VII coincides with peak for 2,4-dichloro-6-(trichloromethyl)-pyridine present during early stages of reaction.
**2,3,4-trichloro-6-(trichloromethyl)pyridine.
***Not analyzed.

TABLE J

Temperature: 200° Catalyst: 7.0 mole % Fe
Pressure: 110 psig Vent Gas Flow: 150 ml/min.

| Sample | Time (hr) | FeCl$_3$ | (I) | (II) | (III) | (IV) | (V) | (VI) | *(VII) | **2,3,4 |
|---|---|---|---|---|---|---|---|---|---|---|
| 0 | 0 | — | 92.2 | .3 | — | — | .2 | — | 5.7 | — |
| 1 | 12 | 5.3 | 31.9 | 28.1 | 11.6 | 1.3 | 1.0 | .2 | 4.1 | 1.1 |
| 2 | 24 | 4.9 | 3.5 | 45.3 | 14.3 | 7.5 | 7.2 | .6 | 2.4 | 3.0 |
| 3 | 36 | 5.0 | .5 | 26.3 | 3.7 | 24.6 | 19.3 | 2.2 | 4.1 | 2.9 |
| 4 | 48 | 3.5 | .2 | 8.3 | .6 | 35.5 | 28.5 | 4.4 | 9.3 | 1.7 |
| 5 | 60 | 4.1 | — | 1.0 | .1 | 22.5 | 33.8 | 4.3 | 20.2 | .4 |
| 6 | 72 | 2.9 | — | .2 | — | 12.6 | 29.0 | 3.4 | 39.3 | .2 |

*G.C. peak for VII coincides with peak for 2,4-dichloro-6-(trichloromethyl)pyridine present during early stages of reaction.
**2,3,4-trichloro-6-(trichloromethyl)pyridine.

TABLE K

Temperature: 200° Catalyst: 7.0 mole % Fe
Pressure: 200 psig Vent Gas Flow: 150 ml/min.

| Sample | Time (hr) | FeCl$_3$ | (I) | (II) | (III) | (IV) | (V) | (VI) | *(VII) | **2,3,4 |
|---|---|---|---|---|---|---|---|---|---|---|
| 0 | 0 | — | 92.2 | .3 | — | — | .2 | — | 5.7 | — |
| 1 | 6 | 4.7 | 30.4 | 33.0 | 13.1 | 1.8 | 1.5 | .3 | 4.0 | 1.2 |
| 2 | 12 | 4.8 | 4.7 | 46.1 | 14.0 | 5.9 | 7.2 | .5 | 2.5 | 2.8 |
| 3 | 18 | 4.9 | 1.9 | 42.9 | 10.0 | 10.4 | 12.1 | .8 | 2.5 | 3.3 |
| 4 | 24 | 4.7 | .5 | 30.3 | 4.0 | 21.0 | 20.1 | 1.8 | 3.7 | 3.0 |
| 5 | 30 | 3.6 | .4 | 15.0 | 1.0 | 30.4 | 30.3 | 3.2 | 7.3 | 2.5 |
| 6 | 36 | 2.9 | .3 | 5.8 | .3 | 28.2 | 36.3 | 3.6 | 12.1 | 1.5 |
| 7 | 42 | 1.8 | — | 2.4 | .1 | 25.3 | 40.8 | 3.9 | 19.8 | .9 |

*G.C. peak for VII coincides with peak for 2,4-dichloro-6-(trichloromethyl)pyridine present during early stages of reaction.
**2,3,4-trichloro-6-(trichloromethyl)pyridine.

The foregoing Tables A–K indicate that varying amounts of desired products (II) through (VII) can be prepared in batch reactions at various pressures, temperatures and catalyst concentrations and indicate the effect of varying one or more of said parameters. Referring particularly to the four specific embodiments of the invention as delineated in the foregoing specification, it is apparent that the desired products (II)–(VII) can be obtained in good yields under the general reaction conditions of the present invention. While data on production of several products is noted in the Tables, it will be apparent to those skilled in the art that the batch reactions can be terminated whenever optimum amounts of a desired product have been obtained and such product thereafter recovered.

Thus, as noted in Table A, optimum amounts of products (II) and (III) can be obtained at 200° C. and atmospheric pressure after a period of about 18–24 hours when using a high (10 mole %) amount of catalyst, although use of such a high catalyst concentration results in undesirably high levels of tar (in excess of about 10 wt. %) in the product distillation bottoms. However, optimum yields of such products can also be obtained with the use of only about 2.0 mole % catalyst, thus minimizing undesired tar build-up, by increasing the pressure, although a longer reaction period of about 48 hours is required. Table B (see also FIG. 3), sample number 2, demonstrates such effect. The effect of further increasing the pressure parameter on the reaction time is shown in Table C, sample 2, about the same optimum amounts of (II) and (III) as obtained in Tables A and B being obtained in a reaction period of about 24–36 hours. Tables D and G indicate that longer reaction periods are also needed to obtain optimum amounts of (II) and (III) when reaction temperatures in the lower end of the operable temperature range are used, even where high pressures and increased catalyst amounts are employed. However, a comparison of data in Tables D and E indicates that the reaction rate is more than doubled as a result of increasing the temperature about 15° C. and/or doubling the catalyst concentration. The effect of temperature increase on reaction rate under the same pressure and catalyst conditions as in Table E is readily apparent from the data in Table F (sample number 1) wherein a short reaction period of only about 12 hours results in optimum production of (II) and (III). The effect of doubling the catalyst from about 2 to about 4 mole % under the same temperature and pressure conditions is also readily apparent from a comparison of Table C (samples 3-4) and Table F (sample 1), the reaction rate also being more than doubled.

Similar results are also seen from a comparison of data in Tables H-K, wherein the pressure and temperature paramters were varied while the catalyst amount was kept constant.

As to the second embodiment of the invention, e.g., the preparation of product (IV) from (I), the same general observations as noted above can be drawn from the data of Tables A-K. Optimum operating conditions are indicated by data in Tables I and K, particularly those noted in Table I.

Likewise, the effects of pressure, temperature and catalyst amounts on the preparation of (V) from (I) are as noted above, with the conditions of Tables F and K resulting in the shortest reaction periods for the production of optimum amounts of product (V).

The foregoing examples illustrate the batchwise preparation of various chlorinated pyridine products. The process can, however, be conducted on a recycle basis. The following example illustrates the preparation of product, starting with substantial pure starting material (I), and illustrates that still bottoms containing original catalyst can be recovered from the distillation of the desired product and recycled, with little loss of catalyst activity, with make-up starting material (I).

EXAMPLE 3

A pilot-plant chlorination system similar to that employed in Example 2 is utilized, the essential difference being the introduction of chlorine gas to the vapor phase above the liquid starting material (I). In such operation, 261 pounds of a molten 2-chloro-6-(trichloromethyl)pyridine starting material was pumped into a warmed (100° C.) Pfaudler reactor having a stirrer and the system purged with $N_2$. 1.3 pounds of iron powder, as the catalyst, was added to the reactor and the flow of chlorine gas (at 100 psig) into the reactor vapor space was commenced. The temperature of the reactor was slowly raised to about 190° C. over a period of about 18 hours, and the reactor then pressured to about 200 psig. The reaction temperature during the rest of the reaction period was maintained at about 200° C. Samples are periodically taken and analyzed to monitor the course of the reaction. The reaction is terminated by cutting the heat to the reactor and allowing the pressure to drop to atmospheric. The reactor and lines are then flushed with $N_2$ and the reactor contents removed and subjected to a vacuum for about 12 hours to remove residual $Cl_2$, HCl and $CCl_4$. The contents are then distilled at reduced pressure (about 20 mmHg.) and the tetra (V) and penta (VII) products removed over a period of about 20 hours. The still bottoms are collected for recycle experiments. Results obtained as a result of following the above procedures are set forth in the following Table L and are illustrated in FIG. 4 hereof:

TABLE L

Temperature °C.* Catalyst: 2 mole % Fe
Pressure: 200 psig Vent Gas Flow: 80-85 Vol. % $Cl_2$

| Sample | Time (hr) | FeCl$_3$ | (I) | (II) | (III) | (IV) | (V) | (VI) | (VII)** |
|---|---|---|---|---|---|---|---|---|---|
| 0 | 0 | — | 87.4 | 1.2 | .3 | — | 1.3 | — | 5.7 |
| 1 | 10.2 | — | 67.1 | 15.5 | 6.0 | .4 | .7 | — | 5.4 |
| 2 | 15.2 | — | 57.1 | 23.3 | 8.7 | 1.2 | .5 | — | 5.2 |
| 3 | 18.0 | — | 50.5 | 27.9 | 10.1 | 1.0 | .6 | .4 | 5.0 |
| 4 | 26.0 | — | 22.5 | 45.0 | 15.4 | 2.2 | 2.5 | .4 | 4.3 |
| 5 | 30.0 | — | 10.3 | 52.0 | 16.8 | 3.3 | 5.2 | .4 | 3.7 |
| 6 | 34.0 | — | 2.5 | 54.4 | 16.2 | 5.9 | 9.5 | .5 | 3.0 |
| 7 | 38.0 | — | .4 | 50.0 | 12.6 | 11.5 | 14.2 | .8 | 2.7 |
| 8 | 42.0 | — | — | 41.8 | 8.8 | 18.5 | 18.0 | 1.7 | 3.4 |
| 9 | 47.0 | — | — | 30.6 | 5.0 | 25.6 | 23.2 | 2.2 | 4.9 |
| 10 | 52.0 | — | — | 21.8 | 3.0 | 28.7 | 28.4 | 2.6 | 6.7 |
| 11 | 56.0 | — | — | 13.6 | 1.6 | 31.2 | 32.6 | 3.3 | 9.2 |
| 12 | 60.0 | — | — | 7.3 | .7 | 31.0 | 36.0 | 3.7 | 12.6 |

*Temperature Profile
0-18 hr. 190°
18-end 200°
**G.C. peak for VII coincides with peak for 2,4-dichloro-6-(trichloromethyl)pyridine present during early stages of reaction.

A portion (536 grams) of the still bottoms remaining after distillation and removal of products V and VII from the product mixture noted in Sample No. 12 in Table L above was mixed with 536 grams of starting material (I) (about 92% 2-chloro-6-(trichloromethyl)pyridine) to give the recycle seed starting material mix noted as sample 0 in Table M below. No additional catalyst was added, the catalyst being that contained in the recycle still bottoms. The seed starting material was then chlorinated utilizing the equipment and procedures of Example 2. The results obtained are set forth in Table M below and are illustrated in FIG. 5.

TABLE M

Temperature: 200° C. Catalyst: 1 mole % Fe
Pressure: 200 psig Vent Gas Flow: 150 ml/min.

| Sample | Time (hr) | (I) | (II) | (III) | (IV) | (V) | (VI) | *(VII) |
|---|---|---|---|---|---|---|---|---|
| 0 | 0 | 45.1 | 4.8 | .1 | 28.4 | — | 4.8 | 12.3 |
| 1 | 9 | 18.5 | 21.7 | 7.9 | 16.6 | 8.6 | 1.9 | 12.1 |
| 2 | 20 | 2.2 | 30.5 | 10.7 | 12.2 | 15.8 | 1.1 | 12.9 |
| 3 | 25 | .1 | 25.1 | 6.7 | 18.9 | 20.1 | 1.7 | 13.7 |
| 4 | 33 | — | 17.2 | 3.6 | 22.9 | 24.9 | 2.6 | 16.1 |
| 5 | 36 | — | 11.5 | 1.9 | 24.1 | 28.0 | 3.0 | 18.0 |

*G.C. peak for VII coincides with peak for 2,4-dichloro-6-(trichloromethyl)pyridine present during early stages of reaction.

The foregoing data illustrate the advantage realized in preparing desired product II by starting with a recycle seed material as well as the ability to recycle catalyst with little loss of activity.

The process of the present invention can also be carried out on a continuous recycle basis to prepare the various products and is the preferred mode for preparing symmetrical tetrachloropyridine (V). Such process comprises the continuous chlorination of a catalyzed liquid phase reaction mass comprising 2-chloro-6-(trichloromethyl)pyridine reaction at temperatures of at least about 160° C. and at pressures of from about atmospheric to about 220 psig or more. The reaction is carried out in a series of reactors for a period of time sufficient to obtain a desired amount of product (V). When such concentration thereof has been reached, the reaction mass is removed from the last reactor and the desired product obtained by fractional distillation of the reaction mass, the still bottoms or a portion thereof being recycled to the first reactor to comprise part of the feed thereto. The overheads can be condensed and the by-products recovered. Preferably, the reaction temperature is from about 100° to about 210° C., the reaction pressures are from about 190 to about 220 psig and the catalyst amount ranges from about 1.0 to about 10 mole %. A reaction temperature of about 200° C., a reaction pressure of about 200 to about 220 psig, and a catalyst amount of about 1 to about 5 mole % are preferred; temperatures and catalyst amounts in excess of these preferred ranges, while operable, tend to cause an undesired increase in tar build-up, which has a detrimental effect on the production of the desired product.

The continuous cyclical process will be described with reference to the preparation of preferred product (V) under preferred conditions and with the reaction scheme noted in FIG. 1, which is presently considered the best mode for the continuous preparation of product (V). It is to be understood, however, that the cyclical process can be used to prepare other products of the invention if so desired.

In the flow sheet of FIG. 1, the molten 2-chloro-6-(trichloromethyl) pyridine feed containing the catalyst is introduced via line 11 and mixed with recycle still bottoms returning via line 25 and the mixture is pumped (not illustrated) to heated reactor 12 and reacted with vaporized chlorine (vaporizer not illustrated) fed through line 14 to the bottom of reactor 12 from chlorine source 13 to form a chlorinated reaction mixture. The chlorinated reaction mixture flows by gravity overflow from reactor 12 to reactor 16 via line 15 where it is further reacted with chlorine fed to the bottom of reactor 16 through line 17. The chlorinated reaction mixture from reactor 16 is likewise fed through line 18 to reactor 19 and further reacted with chlorine fed to reactor 19 through line 20. The chlorinated reaction mixture is then passed from reactor 19 to a stripper column (not illustrated) where light overheads (CCl$_4$, HCl, Cl$_2$) are removed, and then to distillation unit 22 through line 21, wherein additional volatile overheads are removed via line 23 and a mixture containing the desired product recovered through line 24. This mixture can be further distilled to obtain product (V) in high purity if desired. The still bottoms comprising catalyst, tars and other organics, e.g., products (II), (IV), etc., are removed from the bottom of unit 22 and a portion thereof can be transferred as a recycle stream via line 25 to feed line 11. Each of reactors 12, 16 and 19 are vented (26a, 26b and 26c, respectively) for release of excess Cl$_2$ and other volatile by-products. Monitoring of the vent gases also serves as a means to follow the course of the reaction. Catalyst can be separately added to reactor 12 if so desired (not illustrated) and the amount of tar in the recycle stream can also be controlled by a bleed valve on line 25 (not illustrated). The number of reactors is not considered to be critical and fewer or greater numbers of reactors can be used, the conditions and average residence time for each reactor being accordingly adjusted for the product(s) desired and temperature/pressure conditions employed.

Initially, the reaction can be commenced by feeding a composition comprising about 90 weight percent (wt. %) or more of the 2-chloro-6-(trichloromethyl)pyridine starting material in the liquid state (at about 75° C.) to reactor 12 along with about 2 mole % anhydrous ferric chloride catalyst and an excess amount of chlorine to provide about 70% Cl$_2$ in the vent gases. The reaction mass is initially heated at about 190° C. at a pressure of about 200 psig for a period of about 18 hours. Thereafter, the reaction temperature is raised to about 200° C. and the catalyzed liquid phase reaction mass passed from reactor 12 through each of succeeding reactors 16 and 19, each maintained at about 200° C. and about 200 psig, with excess Cl$_2$ fed to each. However, since the initial conversion of starting material (I) to products (II) and (III) is a slow process, it is preferred that a seed starting material comprising the catalyst and about 30 wt. % 2-chloro-6-(trichloromethyl)pyridine (I), about 40 weight % product (II) and (III) and about 20 wt. % (IV), 10% other chlorinated pyridine products be charged to reactor 12 on a continuous basis and the catalyzed liquid reaction mass subjected to chlorination at about 200° C. and about 200 psig as it passes successively through each of the 3 reactors. The Cl$_2$ pressure and temperature can be varied from one reactor to another if necessary to maintain the reaction in a steady state. While the sparging of the chlorine into the reaction mass provides agitation thereof, the reaction mass can also be stirred and agitation is preferably obtained by use of pump means to pass the reaction mass to each of the reactors. The average residence time in each reactor is from about 18 to about 22 hours.

The reaction mass from reactor 19 is continuously removed, stripped of light overheads and then distilled in distillation column 22, from which the desired product (V) is recovered along with (VII). A predominate amount of about 80–90% of the product stream recovered (optimally, about 40% by weight of the reaction mass) is desired product (V) while about 10–20% is mostly product (VII). About 60% of the reaction mass comprises by-products HCl, Cl$_2$ and other products of Formula A, which are also separated from the desired products, and the tars (tars being about 1–5 weight % based on starting material). The still bottoms and some tar are recycled to reactor 12 along with an appropriate amount of make-up feed and additional catalyst (if needed) to maintain the desired starting material composition. The best method of adding make-up catalyst to the molten recycle feed stream comprises adding iron powder to molten product (II) (up to 10–15 wt. % iron based on product (II)) and then chlorinating the mixture as soon as possible. The chlorination is carried out with agitation at about 5–10 psig and at temperatures below about 150° C., preferably at or below about 100° C., until a homogeneous mixture is obtained. An exotherm normally results upon chlorination. For example, addition of about 0.2 mole/hr. of Cl$_2$ to a typical recycle stream at about 100° C. causes an exotherm of about 30°–40° C. over a period of about 30 minutes, the final temperature being about 135°–140° C. with a chlorination period of about 1.5–2 hours being required to obtain a homogeneous mixture, which can then be mixed in appropriate amounts with other recycle and fresh feed streams to form the desired starting material mixture. The products obtained from the distillation column may be further purified by fractional distillation, recrystallization, etc., procedures.

The foregoing continuous recycle embodiment is illustrated in the following Example 4.

EXAMPLE 4

A continuous, recycle process utilizing a reactor scheme substantially as set forth in FIG. 1 was carried out over a prolonged period to study the effects of tar build-up upon the rate of production of symmetrical tetrachloropyridine (V). Three, one-gallon capacity nickel reactors were utilized with the feed starting material, comprising recycle still bottoms and make-up 2-chloro-6-(trichloromethyl)pyridine (I) starting material (about 30 wt. % total of (I) in the feed to the first reactor) and catalyst as needed, being fed at a rate of 3 ml/min. The catalyst amount was maintained at a level of about 1.6 mole %, while the temperature and pressure in each of the reactors was maintained at about 200° C. and about 200 psig, respectively. The average residence time of the reaction mass being chlorinated in each reactor was about 20 hours, the total residence time in the three reactors being about 60–64 hours before the reaction mass was withdrawn and distilled. The continuous recycle process was continued for a period of 62 days and the wt. % of tar versus desired product (V) monitored by analysis of the product material obtained from the last reactor. The results of such operations were plotted and are noted in the graph of FIG. 6. As can be seen from FIG. 6, the build-up in tar concentration the first 20 days of operation from 1 to about 4 wt. % was very detrimental to the production of desired product (V), decreasing the level thereof from a high of nearly 40 wt. % to about 20 wt. %. Temporarily decreasing the tar level in the recycle stream and hence the starting feed material from a high of 6 wt. % to about 1 wt. % over a period of about 10 days resulted in increased levels of product (V), the level of product (V) stabilizing at about 25–28 wt. % as the tar level in the reaction mass was allowed to again increase to a level of about 3 wt. %.

The foregoing example illustrates the continuous, recycle embodiment of the invention and demonstrates the detrimental effect of high tar levels in the reaction mass.

While the foregoing three-reactor system is noted as the best mode contemplated for carrying out the invention in preparing preferred product (V), the best mode now known for carrying out the invention comprises a very similar process wherein a series of four vented reactors is used for the continuous process. In carrying out the same, a molten feed material (a seed feed material as previously described herein) is mixed with an appropriate amount of a catalyst stream (prepared by chlorinating a mixture of iron powder in molten product (II) as noted in Example 3) to form a reaction mass in the first reactor of the series containing about 2 mole % FeCl$_3$. The reaction mass is pumped through each of the four reactors and is subjected to chlorination in each of the four reactors at a temperature of about 200° C. and a pressure of about 200 psig. The chlorine (in excess molar amounts) is sparged into the molten reaction mass in each reactor at a chlorine pressure of about 230 psig. The average residence time of the reaction mass in each reactor is about ten hours, giving an average total residence time in the reactor system of about 40 hours. The last of the reactors is preferably separately vented in order to maintain good control over the final product mix therein.

The product reaction mass exiting the reactor comprises optimum amounts of from about 25–30 wt. % desired product (V) and about 5–10% wt. of product (VII), the remainder of the reaction mass exiting the reactor comprising HCl, Cl$_2$, CCl$_4$, products (II), (III), (V) and (VII), and by-product tars. The reaction mass is separated into its desired components by using conventionally available stripper and distillation techniques and equipment. In such operation, the reaction mass is passed through two strippers to remove CCl$_4$, HCl and Cl$_2$. HCl is injected into the second stripper to insure complete removal of Cl$_2$ before the reaction mass is passed through a vacuum distillation column, where the desired product (V), along with product (VII), some of product (II) and other light organic materials, is recovered as overheads, with the still bottoms comprising catalyst, tars and some of products (II) and (IV). A portion of the still bottoms can be recycled as part of the make-up feed used to mix with starting material (I) in preparing the seed feed material to the first reactor. The overhead stream can be subjected to one or more further vacuum distillation columns to obtain product (V) in the purity desired.

EXAMPLE 5

In other operations utilizing procedures substantially similar to Example 1 and 2 hereof, additional catalysts were evaluated for use in the present invention. In such operations, the chlorination of the starting material (I) (about 93% by weight of 2-chloro-6-(trichloromethyl)-pyridine) was carried out at atmospheric pressure at a temperature of about 200° C. and a catalyst concentration of about 5 mole %.

In one particular set of operations, the wt. % of starting material (I) remaining after 20 hours, hours to achieve maximum concentration of products (II) and (IV), and wt. % of (V) after 70 hours were determined with tungsten, molybdenum, tantalum and niobium catalysts and the results are as follows:

TABLE N

| Catalyst | Mole % | I Wt. % | II Hours | IV Hours | V Wt. % |
|---|---|---|---|---|---|
| WCl$_6$ | 5 | <1 | 5 | 55 | 33 |
| MoCl$_5$ | 5 | <1 | 5 | 45 | 28 |
| MoCl$_3$ | 6.1 | <1 | 5–10 | 45 | 20 |
| MoOCl$_4$ | 5 | <1 | 3 | ~40 | 30 |
| TaCl$_5$ | 5 | <1 | 48 | 48 | 17 |
| NbCl$_5$ | 5 | 18 | 45 | >70 | 7 |

In other similar operations, the following area % of (I), (II), (III) and (IV) were obtained with other catalysts after the reaction times indicated:

TABLE O

| Catalyst | MOle | Hours | I | II | III | IV |
|---|---|---|---|---|---|---|
| — | — | 0 | 93.3 | 0.3 | — | — |
| Aluminum | 5 | 18 | 78.1 | 8.6 | 3.6 | .3 |
| *Aluminum | 5 | 24 | 67.2 | 13.3 | 3.8 | .7 |
| Zinc (Metal) | 5 | 18 | 88.1 | 3.1 | 1.5 | .1 |
| Zinc (Dust) | 5 | 24 | 84.1 | 5.0 | 2.4 | .3 |
| **RuCl$_3$ | 6 | 48 | 8.1 | 48.8 | 5.1 | 7.0 |

*1 mole % I$_2$ added.
**Ruthenium Trichloride.

EXAMPLE 6

Other operations utilizing the procedures of Example 2 were carried out, data from additional runs using aluminum metal (2 mole %) and tantalum pentachloride (2 mole %) being presented in the following Tables P and Q, respectively:

TABLE P

Temperature: 200° Catalyst: 2.0 mole % Al
Pressure: 200 psi Vent Gas Flow: 150 ml/min.

| Sample | Time (hr) | (I) | (II) | (III) | (IV) | (V) | (VI) | *(VII) |
|---|---|---|---|---|---|---|---|---|
| 0 | 0 | 92.0 | .4 | — | — | .1 | — | 6.0 |
| 1 | 5 | 69.4 | 14.1 | 3.1 | .4 | .2 | .1 | 6.1 |
| 2 | 12 | 50.2 | 28.7 | 5.9 | 1.2 | .8 | .3 | 6.2 |
| 3 | 18 | 38.6 | 36.5 | 6.7 | 1.4 | 1.4 | .3 | 6.1 |
| 4 | 24 | 29.8 | 44.0 | 7.9 | 1.6 | 2.4 | .3 | 6.0 |
| 5 | 36 | 10.6 | 53.6 | 8.9 | 3.5 | 6.7 | .4 | 4.8 |
| 6 | 48 | 3.7 | 56.8 | 7.4 | 4.0 | 11.3 | .3 | 3.6 |
| 7 | 60 | .3 | 46.8 | 3.8 | 10.4 | 18.0 | 1.1 | 3.5 |
| 8 | 68 | .3 | 40.8 | 2.2 | 13.2 | 23.4 | 1.4 | 4.6 |

*G.C. peak for VII coincides with peak for 2,4-dichloro-6-(trichloromethyl)pyridine present during early stages of reaction.

TABLE Q

Temperature: 200° C. Catalyst: 2 mole % TaCl₅
Pressure: 200 psi Vent Gas Flow: 150 ml/min.

| Sample | Time (hr) | (I) | (II) | (III) | (IV) | (V) | (VI) | *(VII) |
|---|---|---|---|---|---|---|---|---|
| 0 | 0 | 92.2 | .3 | — | — | .2 | — | 5.7 |
| 1 | 4 | 51.7 | 23.0 | 8.6 | 1.0 | .5 | .2 | 5.1 |
| 2 | 11 | 19.8 | 42.5 | 13.2 | 2.5 | 1.6 | .2 | 3.4 |
| 3 | 18 | 6.9 | 50.5 | 14.2 | 3.7 | 4.5 | .2 | 2.7 |
| 4 | 24 | 0.8 | 51.2 | 12.4 | 7.8 | 9.1 | .5 | 2.2 |
| 5 | 30 | — | 39.2 | 6.3 | 19.8 | 14.0 | 1.5 | 2.7 |
| 6 | 36 | — | 25.2 | 2.4 | 27.4 | 20.1 | 2.2 | 4.4 |
| 7 | 42 | — | 14.0 | .7 | 31.6 | 24.9 | 3.0 | 7.2 |
| 8 | 46 | — | 9.0 | .1 | 29.8 | 31.9 | 3.0 | 10.6 |

*G.C. peak for VII coincides with peak for 2,4-dichloro-6-(trichloromethyl)pyridine present during early stages of reaction.

EXAMPLE 7

In additional operations utilizing procedures substantially similar to Example 2 hereof, other catalysts were evaluated for use in preparing products described herein. In such operations, the chlorination of molten starting material (I) (about 92% by weight 2-chloro-6-(trichloromethyl)pyridine) was carried out at a temperature of about 200° C. and a pressure of about 200 psig, with a Cl₂ vent gas flow of about 150 ml/min. As a result of carrying out such operations at a catalyst amount of 2 mole %, the following catalysts were indicated as being effective in catalyzing the starting material to one or more of the products of the present invention: tellurium tetrachloride, aluminum powder, iron powder, ruthenium trichloride, molybdenum pentachloride, niobium pentachloride, tungsten hexachloride, vanadium trichloride, chromium trichloride, copper chloride, zinc chloride and cobalt chloride.

Although the invention is described with respect to specific embodiments and modifications, the details hereof are not to be construed as limitations except to the extent indicated in the following claims.

What is claimed is:

1. A process for preparing substituted pyridines of the formula:

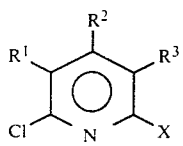

(A)

wherein X represents chloro or —CCl₃, $R^1$, $R^2$ and $R^3$ each independently represent chloro or H, with the proviso that when X is —CCl₃, at least one of $R^1$, $R^2$ or $R^3$ is always Cl and with the further proviso that when X is chloro, one of $R^1$ and $R^3$ is always chloro, which comprises reacting a chloro-substituted 6-(trichloromethyl)pyridine reactant of the formula:

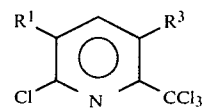

(B)

wherein $R^1$ and $R^3$ represent chloro or H, in the liquid state, with chlorine, said reaction being carried out at a temperature of at least about 160° C. in the presence of a Lewis acid type catalyst and an amount thereof effective to catalyze said reaction.

2. The process of claim 1 wherein X is —CCl₃.

3. The process of claim 1 wherein X is Cl.

4. The process of claim 1 wherein superatmospheric pressures are employed.

5. The process of claim 1 wherein X is Cl, $R^1$ and $R^3$ are each Cl and $R^2$ is H.

6. The process of claim 4 wherein X is Cl, $R^1$ and $R^3$ and each Cl and $R^2$ is H.

7. The process of claim 4 wherein the reaction temperature is from about 160° to about 220° C. and the reaction pressure is from about 15 to about 220 or more psig.

8. The process of claim 6 wherein the reaction temperature is from about 160° to about 220° C., the reaction pressure is from about 15 to about 220 psig or more and the catalyst is employed in an amount of from about 1 to about 10 mole percent, based on the amount of said reactant of formula B.

9. The process of claim 8 wherein the reaction temperature is from about 180° to about 210° C. and the reaction pressure is from about 100 to about 220 or more psig.

10. The process of claim 1 wherein the catalyst is a ferric halide.

11. The process of claim 8 wherein a Lewis acid-type catalyst is employed.

12. The process of claim 11 wherein the temperature is at least about 190° C. and the pressure is at least about 190 psig.

13. A process for preparing substituted pyridine products of the formula:

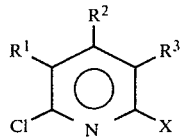

(A)

wherein X represents chloro of —CCl₃, $R^1$, $R^2$ and $R^3$ each independently represent chloro or H, with the proviso that when X is —CCl₃, at least one of $R^1$, $R^2$ or $R^3$ is always Cl and with the further proviso that when X is chloro, one of $R^1$ and $R^3$ is always chloro, which comprises feeding a catalytic amount of a Lewis acid type catalyst and a composition comprising one or more starting materials of the formula:

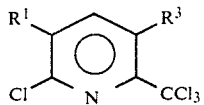

wherein R¹ and R³ are chloro or H, to a first reactor of a reactor series and reacting the same therein in the liquid state with chlorine at temperatures of at least about 160° C., passing the resulting reaction mass through each successive reactor of said series and reacting the same in the liquid state with chlorine in each reactor at a temperature of at least about 160°, the reactions being carried out in said reactor series for a period of time sufficient to form the desired pyridine products in the last reactor of said series, and thereafter recovering said desired pyridine products.

14. The process of claim 13 wherein said desired pyridine products are recovered by distillation and the distillation still bottoms are fed to the first reactor as part of said feed composition.

15. The process of claim 13 wherein X is $CCl_3$.

16. The process of claim 13 wherein superatmospheric pressures are employed.

17. The process of claim 16 wherein the reaction temperature is from about 160° to about 220° C. and the reaction pressure is from about 15 to about 220 or more psig.

18. The process of claim 16 wherein the reaction temperature is from about 160° to about 220° C., the reaction pressure is from about 15 to about 220 psig or more and the catalyst is employed in an amount of from about 1 to about 10 mole percent, based on the amount of said reactant of formula B.

19. The process of claim 16 wherein X is chloro and a Lewis acid-type catalyst is employed.

20. The process of claim 13 wherein the catalyst is a ferric halide.

21. The process of claim 19 wherein the catalyst is a ferric halide.

22. The process of claim 19 wherein the temperature is at least about 190° C. and the pressure is at least about 190 psig.

23. A process for preparing 2,3,5,6-tetrachloropyridine and 2,3,4,5,6-pentachloropyridine which comprises feeding a catalytic amount of a Lewis acid type catalyst and a composition comprising 2-chloro-6-(trichloromethyl)pyridine to a first reactor of a reactor series and reacting the same therein in the liquid state with chlorine at a temperature of at least about 160° C. and at superatmospheric pressures, passing the resulting reaction mass through each successive reactor of said series and reacting the same in the liquid state with chlorine in each reactor under the temperature and pressure conditions of said first reactor, the reactions being carried out in said reactor series for a period of time sufficient to form a reaction mass containing said 2,3,5,6-tetrachloropyridine product and said 2,3,4,5,6-pentachloropyridine product in the last reactor of said series, and thereafter recovering said products from said reaction mass.

24. The process of claim 23 wherein said reaction mass obtained from the last reactor contains optimum amounts of 2,3,5,6-tetrachloropyridine.

25. The process of claim 23 wherein said feed composition comprises from about 10 to about 50 wt. % of 2-chloro-6-(trichloromethyl)pyridine.

26. The process of claim 23 wherein the catalyst is a ferric halide.

27. The process of claim 23 wherein the reaction temperature is from about 160° to about 220° C., the reaction pressure is from about 15 to about 220 psig or more and the catalyst is employed in an amount of from about 1 to about 10 mole percent, based on the amount of said reactant of formula B.

28. The process of claim 23 wherein the reaction temperature is from about 180° to about 210° C. and the reaction pressure is from about 100 to about 220 or more psig.

29. The process of claim 23 wherein the temperature is at least about 190° C. and the pressure is at least about 190 psig.

* * * * *

UNITED STATES PATENT AND TRADEMARK OFFICE
CERTIFICATE OF CORRECTION

PATENT NO. : 4,256,894
DATED : March 17, 1981
INVENTOR(S) : Thomas J. Dietsche; Jim Love It is certified that error appears in the above—identified patent and that said Letters Patent is hereby corrected as shown below:

Column 3, line 16, delete "of" and insert -- or -- ;

Column 3, line 46, insert a comma after "ruthenium";

Column 4, lines 63-68 approximate, the formula III, that portion which reads $CCL_3$ should read $CCl_3$ ;

Column 6, line 38, delete "220" and insert -- 210 -- ;

Column 15, line 6, "parameters" has been misspelled;

Column 16, line 39, delete "as" and insert -- at -- ;

Column 20, Table O, the second column heading should be "Mole %".

Signed and Sealed this

Twenty-ninth Day of September 1981

[SEAL]

Attest:

Attesting Officer

GERALD J. MOSSINGHOFF

Commissioner of Patents and Trademarks

UNITED STATES PATENT AND TRADEMARK OFFICE
CERTIFICATE OF CORRECTION

PATENT NO. : 4,256,894

DATED : March 17, 1981

INVENTOR(S) : THOMAS J. DIETSCHE and JIM LOVE

It is certified that error appears in the above—identified patent and that said Letters Patent is hereby corrected as shown below:

In both Claims 1 and 13, in formula A, that portion of the formula appearing as

" 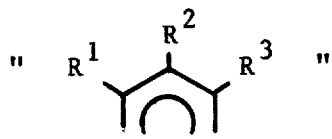 "

should read

-- 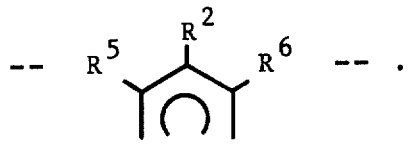 -- .

Column 22, that portion beginning at line 1 with "$R^1$" and ending at line 4 with "$R^3$" and that portion beginning at line 61 with "$R^1$" and ending at line 65 with "$R^3$" should at both occurrences be deleted and the following substituted at each occurrence:

UNITED STATES PATENT AND TRADEMARK OFFICE
CERTIFICATE OF CORRECTION

PATENT NO. : 4,256,894

DATED : March 17, 1981

INVENTOR(S) : THOMAS J. DIETSCHE and JIM LOVE

It is certified that error appears in the above—identified patent and that said Letters Patent is hereby corrected as shown below:

-- $R^5$ is Cl or the same as $R^1$, $R^6$ is Cl or the same as $R^3$, $R^2$ is chloro or H, with the proviso that when X is $-CCl_3$ and $R^2$ is H, then either $R^5$ is not the same as $R^1$ or $R^6$ is not the same as $R^3$ and with the further proviso that when X is chloro, at least one of $R^5$ and $R^6$ -- .

Signed and Sealed this

Thirteenth Day of September 1983

[SEAL]

Attest:

Attesting Officer

GERALD J. MOSSINGHOFF

Commissioner of Patents and Trademarks

UNITED STATES PATENT AND TRADEMARK OFFICE
CERTIFICATE OF CORRECTION

PATENT NO. : 4,256,894
DATED : March 17, 1981
INVENTOR(S) : Thomas J. Dietsche and Jim Love It is certified that error appears in the above—identified patent and that said Letters Patent is hereby corrected as shown below:

In Claim 1, Column 22, line 19, that portion reading "said reaction " should read -- the reaction to replace the trichloromethyl radical with a chloro radical or replace hydrogen substituents with chloro moieties -- .

In Claim 13, Column 23, line 17, immediately after "said series" insert -- by replacing the trichloromethyl radical or hydrogen substituents with chloro moieties -- .

Signed and Sealed this

Sixth Day of December 1983

[SEAL]

Attest:

GERALD J. MOSSINGHOFF

Attesting Officer  Commissioner of Patents and Trademarks